United States Patent [19]
Chandler et al.

[11] Patent Number: 4,936,844
[45] Date of Patent: Jun. 26, 1990

[54] BONE FIXATION SYSTEM

[75] Inventors: Robert W. Chandler, Inglewood, Calif.; John A. Engelhardt, Warsaw, Ind.

[73] Assignee: Boehringer Mannheim Corporation, Indianapolis, Ind.

[21] Appl. No.: 357,034

[22] Filed: May 25, 1989

[51] Int. Cl.$^5$ ............................................... A61F 5/00
[52] U.S. Cl. ........................................ 606/69; 606/72
[58] Field of Search .......... 128/92 R, 92 VK, 92 VZ, 128/92 YF, 89 R, 92 YP; 606/60, 64, 65, 69, 70, 71, 72, 73, 74, 86, 87, 88, 89, 104

[56] References Cited
U.S. PATENT DOCUMENTS

| | | | |
|---|---|---|---|
| 583,455 | 6/1897 | Bush | 128/92 YL |
| 2,494,229 | 1/1950 | Collison | 128/92 R |
| 3,025,853 | 3/1962 | Mason | 128/924 YK |
| 3,716,050 | 2/1973 | Johnston | 606/69 |
| 3,741,205 | 6/1973 | Markolf et al. | 128/92 R |
| 3,824,995 | 7/1974 | Getscher et al. | 128/92 R |
| 3,862,631 | 1/1975 | Austin | 128/92 R |
| 3,955,567 | 5/1976 | Richmond et al. | 128/92 R |
| 4,040,129 | 8/1977 | Steinemann et al. | 623/18 |
| 4,135,506 | 1/1979 | Ulrich | 128/92 VZ |
| 4,565,193 | 1/1986 | Streli | 128/92VK |
| 4,683,878 | 8/1987 | Carter | 128/92 YP |

FOREIGN PATENT DOCUMENTS 0299160  1/1989  European Pat. Off. .......... 128/92 R

OTHER PUBLICATIONS

"Osteotolmy of the Proximal Tibia", pp. 272, 273, from *Manual of Internal Fixation*, by M. E. Muller et al., Springer-Verlag, New York-Heidelberg-Berlin; 1970; 4 pages.

One page from 1982-1985 DePuy catalog entitled "1918-50/59 Duopress TM Osteotomy Blade-Plates".

*Primary Examiner*—Robert A. Hafer
*Assistant Examiner*—Lynda M. Cofsky
*Attorney, Agent, or Firm*—Perman & Green

[57] ABSTRACT

A fixation system for drawing together into engaging relationship mutually opposed fracture surfaces of a pair of bone fragments at a fracture site. An elongated blade with a sharpened leading end is driven into a first bone fragment generally parallel to and spaced from a fracture surface of the first bone fragment. A flange member integral with the blade extends transverse of the blade and overlies the fracture site between the first and second bone fragments. At least one screw fastener with a head and threaded shank extends through an opening in the flange and is threaded into the second bone fragment along an axis which extends away from the blade. With continued tightening of the screw fastener, the head engages the flange and draws the flange against both bone fragments, holds the blade in a deepest seated relationship with the first bone fragment, and imparts a compressive or wedging force to the first and second bone fragments forcing them together at the site of fracture and enabling healing to proceed.

5 Claims, 2 Drawing Sheets

BONE FIXATION SYSTEM

BACKGROUND OF THE INVENTION

1. Field of the Invention

The present invention relates generally to bone surgery and, more particularly, to a fixation system for drawing together into engaging relationship for healing mutually opposed fracture surfaces of a pair of bone fragments at a fractured site.

In instances in which fracture of a bone has occurred or in which surgical osteotomy, that is, a planned fracture, has been performed, it is necessary to join the fragments together in a semi-rigid fashion, to promote rapid healing and eventual union of the bone fragments. The term "semi-rigid" is intended to imply that if too much or too little relative motion between the fragments occurs, eventual mal or non union may result.

In the specific instance of the varus deformed tibia, or bow leggedness, high forces occur in the medial compartment of the knee, resulting in arthritis and pain. Surgical intervention to relieve the arthritic condition requires that a wedge of bone be removed from the tibia in the frontal plane just below the tibial subchondral plate. Once this wedge is removed, the proximal tibial fragment is collapsed upon the distal fragment and the two fragments are fixed with some type of hardware. In this manner, the bow is taken out of the tibia and a uniform load distribution in both departments of the knee results. This causes the arthritic condition in the medial compartment of the knee to abate, and the pain disappears.

2. Description of the Prior Art

The hardware classically employed to fix the fragments in the above described procedure varies depending upon the preference of the surgeon In many instances existing hardware is modified to address the special osteotomy case.

An accepted technique for many years used Steinmann pins and associated external compression clamps This technique is described at pp. 272 and 273 of *Manual of Internal Fixation* by M. E. Muller et al, published in 1970 by Springer-Verlag, New York - Heidelberg - Berlin.

Elongated fixation plates overlying the fracture site have also long been known as evidenced by the patents to Collison, U.S. Pat. No. 2,494,229 and to Markolf et al U.S. Pat. No. 3,741,205.

The coventry staple was designed for wedge osteotomy cases and consists of a metallic flat staple with two prongs. When driven into the collapsed osteotomy site, one prong engages the proximal fragment, and one the distal fragment. Several staples are generally used at spaced locations along the fracture site. While sometimes effective, the conventry staples tend not to compress the fragments together, but only prevent distraction of the collapsed osteotomy site. Further, the cross section of the pointed spikes is quite small. As a result, the spikes have a tendency to tear out of the surrounding bone, which, over time, can lead to loosening of fixity and eventual non-union. An example of an improved surgical staple for joining bone fragments is the patent to Austin, U.S. Pat. No. 3,862,631.

In some cases, a series of cancellous bone screws are threaded into each fragment and surgical wire is wrapped around each screw to cinch down the fragments While this method of fixation often leads to eventual union, it also frequently occurs that the screws tend to cut out and fixity is lost.

Another known method of fixation is provided by means of a bone pin which traverses the fracture as disclosed by the patent to Ulrich, U.S. Pat. No. 4,135,506. While this technique may hold the bone fragments in proper alignment, it does not serve to compress the fragments so as to encourage healing.

In still other instances, elongated plates are provided which extend along and attach to the outer surface of the bone and overlie the fracture but include a component which is driven into at least one of the fragments. Such an arrangement is disclosed in the patents to Getscher et al, U.S. Pat. No. 3,824,995, to Richmond et al, U.S. Pat. No. 3,955,567, and to Streli, No. 4,565,193.

Still another concept used for bone fixation utilizes an elongated plate which extends along and attaches to the outer surface of the bone fragment but includes an element which traverses the fracture. Such a device is disclosed by the patent to Mason, U.S. Pat. No. 3,025,853. A significant drawback of this technique is the requirement for a large incision in order to implant the plate. This calls for a substantial surgical effort and results in a longer healing time and increased trauma to the patient.

In many instances involving all of the foregoing devices, the staples, pins, and plates did not present adequate surface area to the underlying bone resulting in "cut out" and resulting loss of fixity. Furthermore, often times they did not adequately hold the bone fragments together, or provide any way for the surgeon to adjust the amount of compressive force applied to a particular situation.

Recognizing the drawbacks of the various methods and constructions of fixation for unintended fractures as well as for resection osteotomy, an improved system of fixation has been developed which would preclude the associated complications of the known devices and techniques.

SUMMARY OF THE INVENTION

The present invention comprises a bone fixation system which includes a straight flat blade having any one of a variety of lengths depending upon the type and size of the fracture and of the bone fragments. The blade is intended to be driven into one bone fragment in a direction parallel to the fracture. A flange on the end of the blade is bent obliquely in the direction of the leading tip of the blade. One or more holes in the flange project through the flange in a direction away from the closing site of the osteotomy. The osteotomy is collapsed and screws are placed through the holes in the flange and threaded through the bone such that both cortices of the bone are engaged by the screws. The angle of the screws with relation to the blade is such that when the screws are tightened, force is exerted in the direction of pushing the blade deeper into the fragment while simultaneously compressing the osteotomy fragments together. The profile of the blade is comparatively broad. This construction serves to distribute the compressive forces across a large area thereby preventing cut out of the blade through the bone. By bicortical fixation of the screws, significantly improved compression of the fragments can be obtained and opportunity for union of the fragments optimized.

The invention disclosed relates to an improved device for fixation of osteotomy fragments in cases of high osteotomy of the tibia. Nonetheless, the invention is general in scope and its principles can be applied to fractures and osteotomies of any type. The tibial osteotomy case is used for descriptive purposes only.

A significant benefit of the invention resides in the fact that only a relatively small incision is required in order to implant the hardware comprising the invention. This results in less time for healing and reduced trauma for the patient.

Other and further features, advantages, and benefits of the invention will become apparent in the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate one of the embodiments of the invention, and, together with the description, serve to explain the principles of the invention in general terms. Like numerals refer to like parts throughout the disclosure.

DETAILED DESCRIPTION OF THE PREFERRED EMBODIMENT

Figure 1:
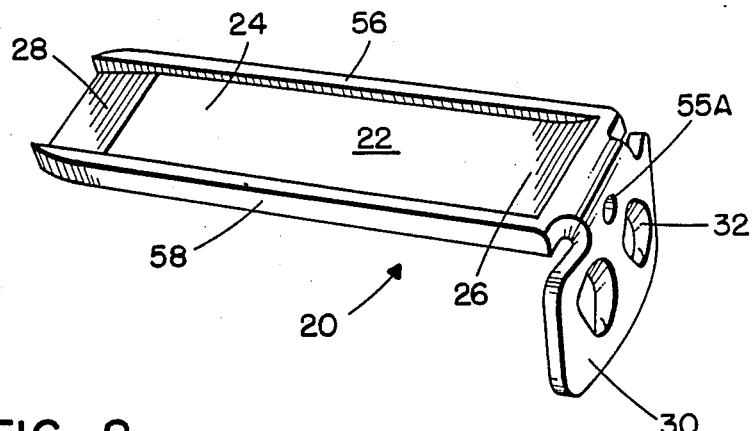
FIG. 1 is a perspective view of an osteotomy plate which comprises one component of the invention.
Figure 2:
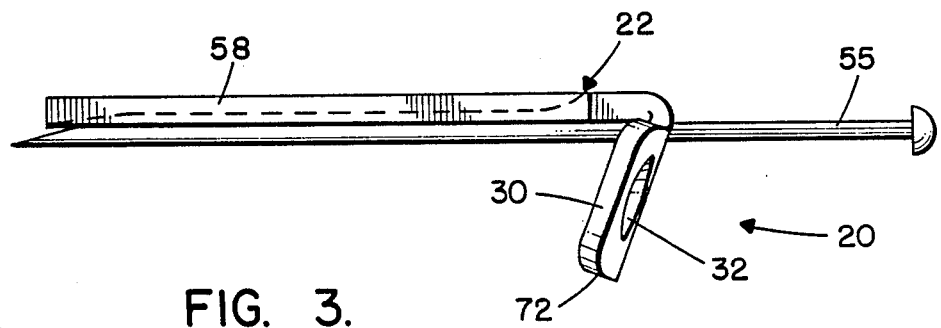
FIGS. 2 and 3 are side elevation and top plan views, respectively, of the osteotomy plate illustrated in FIG. 1.
Figure 3:
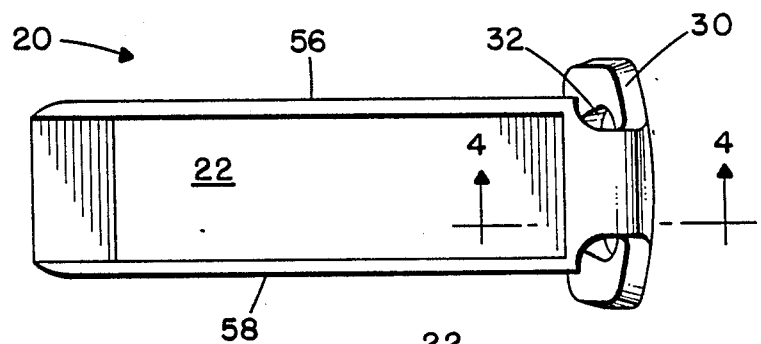

Turn now to the drawings and, initially, to FIGS. 1–3 which illustrate one component of the fixation system embodying the invention. In this regard, the invention comprises an osteotomy plate 20 which includes an elongated blade 22 which is of variable length depending upon the type and location of fracture to be reduced. The blade 22 has a low aspect ratio, that is, it is relatively broad in relation to its length, in order to prevent "cut out". Cut out occurs when the width of a pin, staple, plate, or other fixation device is so relatively narrow that, over time, it cuts laterally through the bone and is eventually dislodged. The blade 22 extends between leading and trailing ends 24 and 26, respectively, and an extremity of the leading end 24 is sharpened as at 28.

Figure 4:
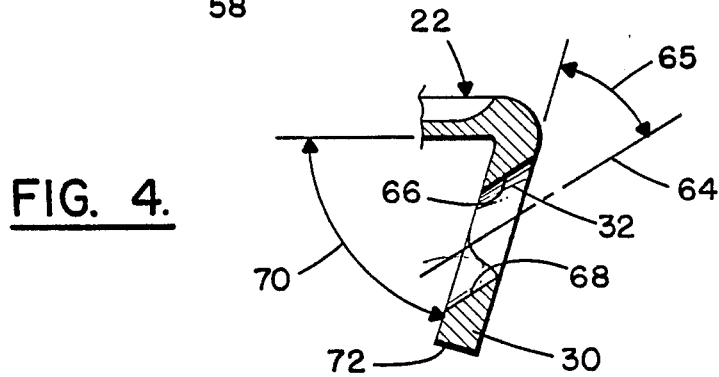
FIG. 4 is a cross section view taken generally along line 4—4 in FIG. 3.

A flange member 30 is integral with the trailing end 26 of the blade 22 and extends transverse of the blade, preferably at an acute angle as most clearly illustrated in FIGS. 2 and 4. A pair of through openings 32 are provided in the flange member 30, each opening intended for reception of a screw fastener 34, (FIG. 6) in a manner which will be more fully described below. While two through openings 32 are provided in the flange member 30, it may indeed have any desired number in keeping with the size of the osteotomy plate 20.

Figure 5:
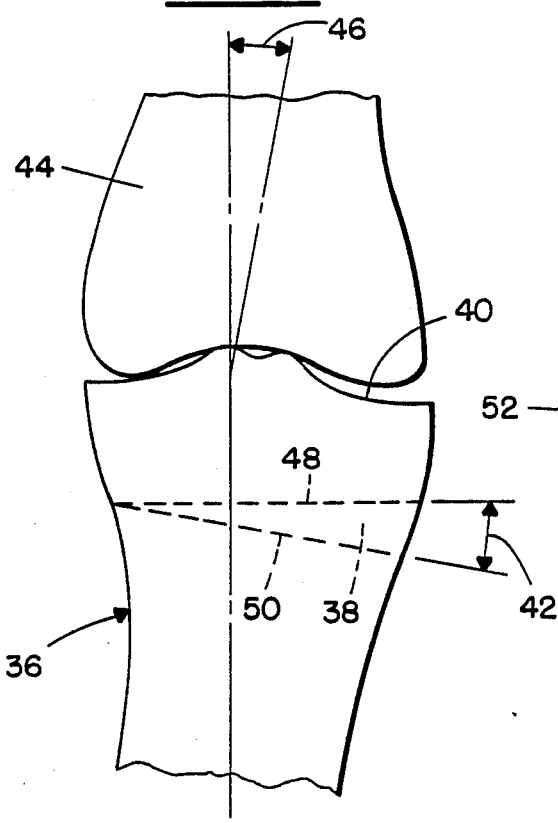
FIG. 5 is a detail front elevation view taken in the region of a knee joint and depicting a varus deformed tibia.
Figure 6:
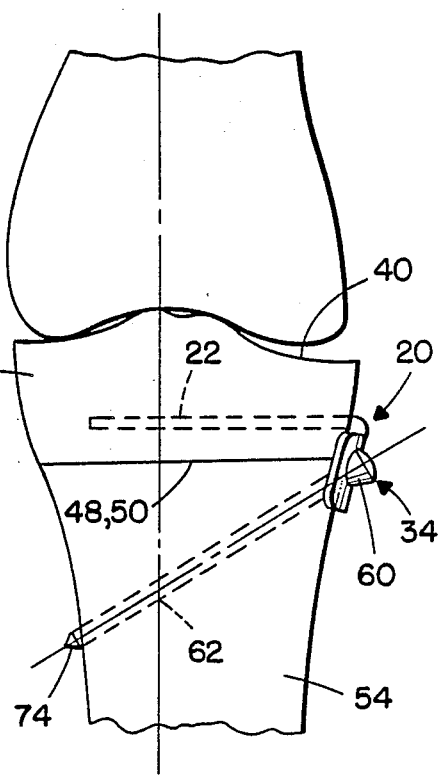
FIG. 6 is a detail front elevation view, similar to FIG. 5, illustrating a corrected tibia following surgery utilizing the fixation system of the invention.

FIGS. 5 and 6 are illustrative of "before" and "after" situations utilizing the fixation system of the invention. FIG. 5 is representative of a varus deformed tibia 36 from which a wedge of bone 38 is to be removed in the frontal plane below the tibial articular surface 40. As seen in FIG. 5, the wedge of bone 38 subtends an angle 42 which, upon removal, enables the femur 44 and the remainder of the skeleton to straighten by a similar angle 46 thereby correcting the condition. The wedge 38 is defined between upper and lower fracture surfaces 48, 50, respectively.

Turning now to FIG. 6 which illustrates the wedge of bone 38 removed and the osteotomy collapsed so that the fracture surfaces 48 and 50 are depicted as being substantially co-planar. Also, as depicted in FIG. 6, the blade 22 of the osteotomy plate 20 has been suitably driven into an upper bone fragment 52 until the flange member 30 engages an outer surface of the upper bone fragment 52 and an adjacent lower bone fragment 54 resulting after removal of the wedge 38.

Prior to driving the blade 22 into the bone fragment 52, it may be desirable to insert a guide pin 55 through a hole 55A in the flange member 30, advance it by and along a lower surface of the blade, then into the bone fragment. As the blade is driven into the bone fragment 52, the guide pin partially supports and at least initially aids in assuring the proper orientation of the blade relative to the fracture surface 48. Thereafter, the guide pin 55 is removed.

Although not necessary, a pair of elongated side rails 56, 58 extend beyond a plane of the blade 22 and are generally coextensive of the blade between its leading and trailing ends 24, 26. Furthermore, the side rails 56, 58 are sharpened at their leading ends in the manner of the sharpened end 28 of the blade 22. The side rails serve to further stiffen the plate 22, to prevent any potential lateral cut-out of the blade through the bone, and aid in guiding the blade into the bone as it is initially implanted.

With the fracture surfaces 48, 50 contiguously oriented as indicated in FIG. 6, a screw fastener 34 is introduced through each of the openings 32 and threadedly advanced into the lower bone fragment 54.

Figure 7:
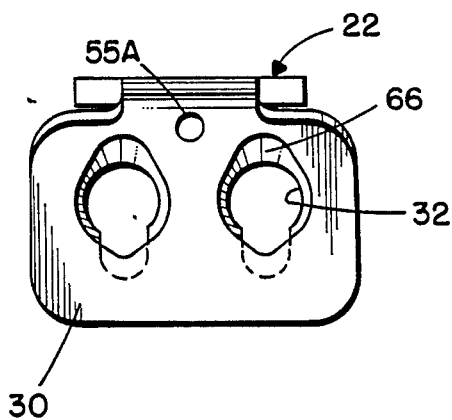
FIGS. 7 and 8 are front elevation and rear elevation views, respectively, of the osteotomy plate illustrated in FIGS. 1–3.
Figure 8:
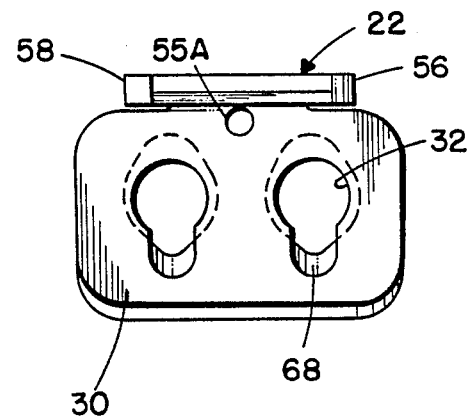

The screw fastener 34 includes a head 60 and a threaded shank 62 extending away from the head in a customary manner. Each through opening 32 has an axis 64, as particularly well seen in FIG. 4, which forms an acute angle 65 with the flange member 30 and extends away from the blade 22 with increasing distance in the direction of the lower bone fragment 54. Each opening 32 is defined by an outwardly facing crescent surface 66 (see FIGS. 4 and 7) nearest the blade 22 and an inwardly facing crescent surface 68 (see FIGS. 4 and 8) farthest from the blade.

Therefore, it is seen that the openings 32 appropriately direct their associated screw fasteners 34 to assure that they advance into the bone fragment 54 in a direction away from the blade 22. With continued advance of the screw fastener into the bone, the head 60 eventually engages the flange 30, as seen in FIG. 6. At this point, continued tightening of the screw fastener forces the flange member 30 firmly against the outer surface of both bone fragments 52, 54 and overlying the site of fracture defined by the fracture surfaces 48, 50. The preferred construction of the osteotomy plate 20 according to which an angle 70 (see FIG. 4) between the plate 22 and the flange member 30 is less than 90°, assures that an extreme edge 72 of the flange member 30 will always oppose, or bear against, the lower bone fragment 54 and thereby prevent soft tissue impingement. Furthermore, the interaction thereby created between the blade 22, the flange member 30, and the screw fastener 34 causes a wedging action which draws the fracture surfaces 48, 50 ever closer to one another with continued tightening of the screw fastener 34. At the same time, a force component urges the blade 22 ever deeper into the upper fragment 52 For maximum effectiveness of the system, a tip end 74 of the screw fastener 34 protrudes from cortical bone at the opposite side of the bone fragment 54.

However, it will be appreciated, as previously noted, that the bone fragments 52, 54 must be joined together in a semi-rigid fashion in order to assure proper healing of the fracture site. By reason of the construction just described, the surgeon is able to apply a selected compressive force to the bone fragments, holding them firmly together at the site of fracture in a selected contiguous relationship, thereby enabling healing to proceed. Thus, the system described enables the surgeon in the operating room to use the fixation system of the invention while simultaneously applying his own subjective judgment for the situation at hand. This ability of the present invention is in contrast to most other known devices, systems, and procedures which require tightening of fasteners to some constant predetermined extent.

While preferred embodiments of the invention have been disclosed in detail, it should be understood by those skilled in the art that various other modifications may be made to the illustrated embodiments without departing from the scope of the invention as described in the specification and defined in the appended claims.

What is claimed is:

1. A fixation system for drawing together into engaging relationship mutually opposed fracture surfaces of a pair of bone fragments at a site of fracture comprising:

an elongated blade extending between leading and trailing ends, said leading end being sharpened to enable said blade to be driven into a first bond fragment generally parallel to and spaced from a fracture surface of the first bone fragment;

a flange member integral with said trailing end of said blade and extending transverse of said blade and positioned to engage the first and second bond fragments and overlie the site of fracture between the first and second bone fragments, said flange member having at least one through opening therein the opening having an axis which extends away from said blade with increased distance into the second bone fragment, the opening being defined by an outwardly facing crescent surface nearest said blade and an inwardly facing crescent surface farthest from said blade;

a screw fastener for reception through each opening in said flange member, said screw fastened having a head and a threaded shank extending away from said head, said screw fastener intended for threaded engagement with the second bone fragment along the axis of the through opening in said flange member away from the site of the fracture and away from said blade with increased distance from said flange member and subject to being tightened until said head engages said flange member, and thereafter, to impart a selected compressive force to the first and second bone fragments causing them to be firmly held together at the site of fracture in a selected contiguous relationship thereby enabling healing to proceed.

2. A fixation system as in claim 1
wherein a plane of said flange member forms acute angle with a plane of said blade.

3. A fixation system as set forth in claim 1
wherein the plane of said flange member is curved so as to conform to an outer surface of the bond fragments.

4. A fixation system as set forth in claim 1
wherein said flange member has an outer surface facing away from the bone fragments and an inner surface engageable with the bone fragments.

5. A fixation system as set forth in claim 1
wherein said blade is substantially flat and includes a pair of elongated side rails extending beyond a plane of said blade, said side rails also extending between leading and trailing ends adjacent, respectively, said leading and trailing ends of said blade and being sharpened at said leading ends.

* * * * *